Figure 1:
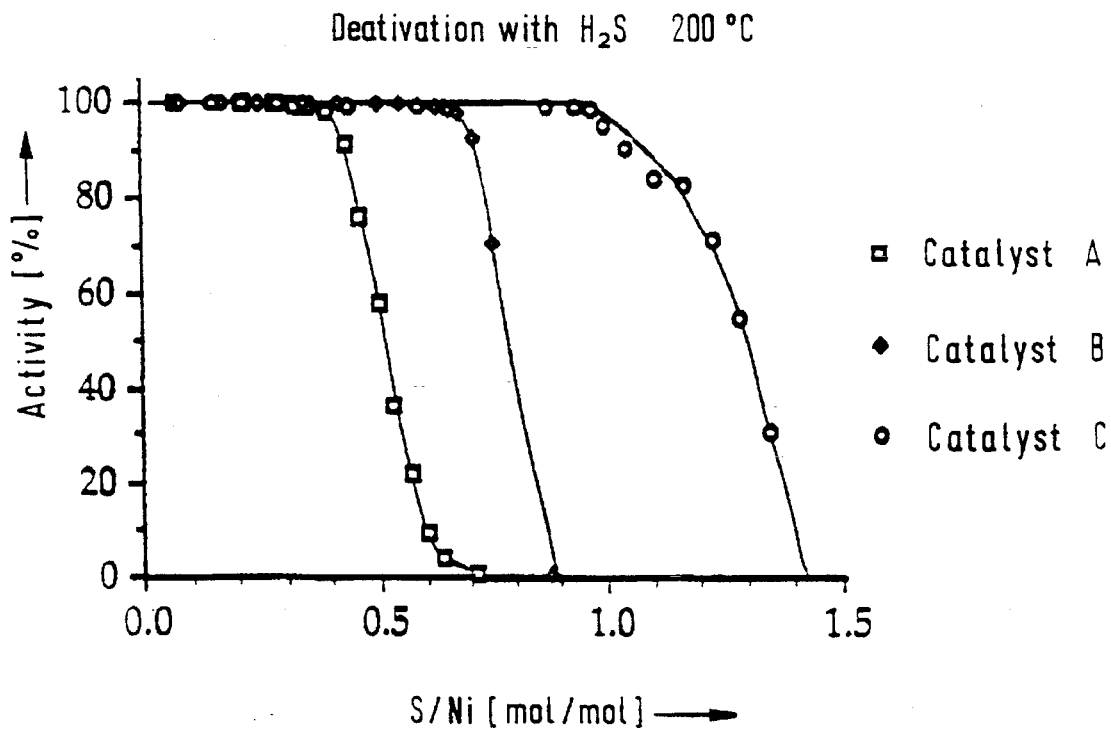

United States Patent [19]

Brahma et al.

[11] Patent Number: 5,482,616
[45] Date of Patent: Jan. 9, 1996

[54] PROCESS FOR HYDROGENATION AND/OR DEHYDROGENATION

[75] Inventors: Nilanjan Brahma, De Meern; John W. Geus, Bilthoven; Eugène G. M. Kuijpers, Apeldoorn, all of Netherlands

[73] Assignee: Engelhard De Meern B. V., De Meern, Netherlands

[21] Appl. No.: 888,187

[22] Filed: May 26, 1992

Related U.S. Application Data

[62] Division of Ser. No. 523,883, May 15, 1990, abandoned.

[30] Foreign Application Priority Data

May 18, 1989 [NL] Netherlands ............................ 8901239

[51] Int. Cl.$^6$ .............................. C10G 45/00; C07C 5/10
[52] U.S. Cl. ..................... 208/143; 208/144; 585/660; 585/662; 585/663; 585/269; 585/270
[58] Field of Search .................................. 585/270, 269, 585/265, 661; 208/143

[56] References Cited

U.S. PATENT DOCUMENTS

| | | | |
|---|---|---|---|
| 3,437,588 | 4/1969 | Kovach et al. ........................ | 208/216 |
| 3,562,800 | 2/1971 | Carlson et al. ........................ | 208/216 |
| 3,912,787 | 10/1975 | Nowack et al. ........................ | 585/270 |
| 3,920,615 | 11/1975 | Huang ................................... | 585/661 |
| 3,997,477 | 12/1976 | Takeuchi .............................. | 252/465 |
| 4,026,823 | 5/1977 | Van Hook et al. ..................... | 252/472 |
| 4,102,822 | 7/1978 | Mulaskey ............................. | 252/465 |
| 4,108,912 | 8/1978 | Takemura et al. . | |
| 4,124,537 | 11/1978 | Gembicki et al. ..................... | 252/465 |
| 4,160,745 | 7/1979 | Murrell et al. . | |
| 4,186,080 | 1/1980 | Mikovsky et al. ..................... | 208/143 |
| 4,251,672 | 2/1981 | Carter et al. . | |
| 4,263,225 | 4/1981 | Carter . | |
| 4,295,818 | 10/1981 | Angwin et al. ........................ | 431/7 |
| 4,420,648 | 12/1983 | Carter et al. . | |
| 4,448,896 | 5/1984 | Kageyama et al. ................... | 502/314 |
| 4,518,709 | 5/1985 | Pellet .................................... | 502/254 |
| 4,734,496 | 3/1988 | Hu et al. . | |
| 4,734,536 | 3/1988 | Nagahara et al. . | |
| 4,791,090 | 12/1988 | Pereira et al. ........................ | 502/263 |
| 5,068,025 | 11/1991 | Bhan . | |
| 5,189,233 | 2/1993 | Larkin ................................... | 585/265 |

FOREIGN PATENT DOCUMENTS

| | | |
|---|---|---|
| 0009068 | 4/1980 | European Pat. Off. . |
| 0091814 | 10/1983 | European Pat. Off. . |
| 0199443 | 10/1986 | European Pat. Off. . |
| 0199509 | 10/1986 | European Pat. Off. . |
| 0314295 | 5/1989 | European Pat. Off. . |
| 2576031 | 7/1986 | France . |

OTHER PUBLICATIONS

"Evaluation of Candidate Solids for High–Temperature Desulfurization of Low–Btu Gases", Phillip R. Westmoreland, et al., Environmental Science & Technology, vol. 10, No. 7, Jul. 1976 pp. 659–661.

Primary Examiner—Helane Myers
Attorney, Agent, or Firm—Weingarten, Schurgin, Gagnebin & Hayes

[57] ABSTRACT

This invention relates to a catalyst for hydrogenation and/or dehydrogenation having an improved resistance against deactivation by sulfur compounds, comprising at least one hydrogenation component, at least one metal-oxide containing component and at least one component acting as a support material, in which at least a part of the hydrogenation component and a part of the metal-oxide containing component are present on said support material as separate particles, the particles of the hydrogenation component and the particles of the metal-oxide containing component being homogeneously distributed in the catalyst.

14 Claims, 2 Drawing Sheets

PROCESS FOR HYDROGENATION AND/OR DEHYDROGENATION

This application is a division of application Ser. No. 07/523,883, filed May 15, 1990 now abandoned.

FIELD OF THE INVENTION

The invention relates to a catalyst for hydrogenation and/or dehydrogenation having an improved resistance against deactivation by sulfur compounds.

BACKGROUND OF THE INVENTION

When hydrogenation and dehydrogenation catalysts are used, often a problem presents itself in that the feedstock comprises sulfur and/or sulfur components, which adversely affects the lifetime of the catalyst. To avoid this problem much attention has been paid to the removal of sulfur compounds from the gaseous or liquid feedstock prior to the hydrogenation and/or dehydrogenation proper. In general sulfur impurities are present in feedstocks as mercaptans or thiophenes, which can be hydrogenated to $H_2S$ using a sulfidized Co-Mo catalyst. This method is also known as hydrodesulfurization (HDS). The $H_2S$ formed may then be removed by reaction with activated zinc oxide, or, after separation and concentration, be processed to elemental sulfur in an organic stripper in a conventional Claus process.

On the other hand, under certain conditions, particularly when the sulfur content of the feedstock is not too high, it is economical not to remove the sulfur compounds prior to the hydrogenation or dehydrogenation process, but to allow a gradual deactivation of the catalyst. After deactivation the catalyst is then replaced.

Since there is a need for processing feedstocks having a higher content of sulfur compounds than has been conventional up to now—which would lead to an unacceptably short lifetime of the catalyst—it is desirable in the process discussed last to have a catalyst system with a reduced sensitivity to deactivation by sulfur compounds.

The object of the invention is therefore to provide a catalyst for hydrogenation and/or dehydrogenation having improved resistance against deactivation by sulfur and/or sulfur compounds. According to the invention such a catalyst comprises at least one hydrogenation component, at least one metal-oxide containing component and at least one support material, at least a part of the hydrogenation component, as well as at least a part of the metal-oxide containing component being present on said support material as separate particles, and the particles of the hydrogenation component and the particles of the metal-oxide containing component being homogeneously distributed in the catalyst. The requirement of homogeneous distribution implies inter alia that the catalyst comprises a support material with particles of a hydrogenation component and particles of a metal-oxide containing component applied to it, with the composition of a relatively small volume part, for instance 1 $mm^3$ or 0.01 $mm^3$, being essentially the same as the total composition of the catalyst. Of course, minor variations may occur in the composition, but should not, preferably, exceed 15%. The distribution may for instance be determined by means of scanning electron microscopy in combination with element analysis.

Surprisingly, it was found that the catalyst according to the invention is eminently suitable for hydrogenation and/or dehydrogenation of organic compounds with sulfur compounds being present in the feedstock. It is particularly surprising that the present catalyst can also be used for feedstocks containing mercaptans and thiophenes, because the known methods of removing sulfur compounds from gases or fluids using metal-oxide containing components are only suitable for the removal of $H_2S$.

For the proper activity of the catalyst according to the invention it is necessary to satisfy the requirement that at least a part of the hydrogenation component and at least a part of the metal-oxide containing component are present on the support material as separate particles. More particularly this means that the hydrogenation component is in direct contact with the metal-oxide containing component only to a very limited extent, if at all. The presence or absence of direct contact can be determined inter alia by means of temperature-programmed reduction and analytic electron microscopy, optionally after reduction of the catalyst.

A feature of the invention is for as small a part as possible of the metal-oxide containing component to be in direct contact with the hydrogenation component. More particularly, it is preferred there is no direct contact at all. One way of determining the extent of direct contact is to compare the activity of the catalyst which contains the metal-oxide containing component with the activity of an otherwise identical catalyst in which the metal-oxide containing component is not present. A suitable test reaction for this purpose is for instance the hydrogenation of benzene.

More particularly, to this end the activity per unit weight of hydrogenation component is determined of a hydrogenation catalyst with and one without a metal-oxide containing component. For a catalyst to be acceptable its activity should not suffer a decrease exceeding 50% as a result of the presence of the metal-oxide containing component, more particularly the decrease should not exceed 30%. In the definition given hereinabove it has been assumed that the measured activity is identical to the chemical reaction rate. In practice this means that the reaction rate should not be limited by diffusion phenomena.

In this connection it is further observed that in certain cases it may be advantageous for the activity to be reduced as a result of the presence of the metal-oxide containing component. For instance in the case of strongly exothermic hydrogenation reactions it is easier to control the reaction with the catalyst according to the invention. In such cases, therefore, it may be useful to accept a stronger decrease of activity than has been presented as advantageous hereinabove.

One of the components of the catalyst is the hydrogenation component. In principle this component may be any metal or any combination of metals which are active in promoting the hydrogenation and/or dehydrogenation of an organic compound. Preferably the hydrogenation component is selected from the group consisting of nickel, copper, platinum, palladium, rhodium, cobalt, ruthenium and mixtures of two or more of these metals. More particularly nickel is used since optimal results are obtained with this metal.

After reduction the catalyst comprises the hydrogenation component in the form of metal particles, the size of the particles of the hydrogenation component, determined by the broadening of the lines of the X-ray diffraction pattern, being between 1 and 40 nm. It is also possible to determine the size of the metal particles using Electron Microscopy, optionally in combination with electron diffraction. The metal-oxide containing component which is used in the catalyst according to the invention, consists in principle at least in part of metal oxide. The oxide or the oxides should satisfy the following two requirements:

1. The metal oxide should not to any considerable extent be reduced to the corresponding metal, either during the activation, in particular during the reduction of the precursor of the hydrogenation component, or under the process conditions.

2. The metal oxide should be capable of reacting to a stable sulfide under the conditions obtaining. Suitable metal oxides that satisfy this requirement are the oxides of inter alia silver, lanthanum, antimony, nickel, bismuth, cadmium, lead, tin, vanadium, calcium, strontium, barium, cobalt, copper, tungsten, zinc, molybdenum, manganese and iron. See also P. R. Westmoreland and D. P. Harrison "Environmental Science and Technology", Vol. 10 (7), pp. 659–661 (1976), in an article entitled "Evaluation of candidate solids for high-temperature desulfurization of low-BTU gases".

In order to satisfy the first requirement the reducibility of the metal-oxide containing component should in general be smaller than the reducibility of the hydrogenation component.

More particularly iron is preferred as a metal for the metal-oxide containing component, since iron satisfies the above requirements under virtually all conditions, and optimal results are obtained with iron oxide as a metal-oxide containing component. The iron present in iron oxide may be bivalent iron and/or trivalent iron. Under hydrogenating conditions the iron-oxide containing component will in general comprise lower oxides than iron(III) oxide, possibly in combination with metallic iron.

The size of the particles of the metal-oxide containing component is within the same limits as those indicated for the hydrogenation component, and the size of the particles may in principle be determined in the same way.

The ratio of hydrogenation component to metal-oxide containing component may vary within very wide limits. In general the extreme limits are determined by the atomic ratios of hydrogenation component to metal-oxide containing component of 1/99 to 99/1. The optimal value is essentially determined by the sulfur content of the feed gas to be treated and the desired lifetime of the catalyst. Generally speaking, a catalyst according to the invention preferably consists as to 2–98 wt % of metal-oxide containing component and, as to the rest, of support material and hydrogenation component put together.

According to the most general embodiment the catalyst may comprise 5–99.9 wt % of support material calculated on the total weight of the support material and the hydrogenation component in reduced form. The amount of hydrogenation component generally depends on the nature and activity thereof. In principle a distinction can be made between noble metals on the one hand, such as platinum, palladium, rhodium and ruthenium, and non-noble metals ("base metals"), on the other, such as nickel, copper and cobalt. When noble metals are used as hydrogenation components, the content will in general be >0.1 wt % and not exceed 10 wt % calculated on the total weight of the support material and the hydrogenation component in reduced form, whereas in the case of non-noble metals the content will in general be larger than 5 wt % and not exceed 95 wt %, calculated on the total weight of the support material and the hydrogenation component in reduced form.

The hydrogenation component and the metal-oxide containing component are applied to a support material, and in principle any support material can be used. As a support material preferably a high-porosity thermostable support material is used. Preferably a support material is used from the group consisting of aluminum oxide, silicon oxide, silicon oxide-aluminum oxide, titanium dioxide, zirconium dioxide, magnesium oxide, mixtures of two or more of these support materials and active carbon. The size of the particles of the support material, which may or may not be porous, is preferably between 0.001 and 200, more particularly between 0.005 and 150 µm.

It is observed that it is not necessary for the particles of the metal-oxide containing component and the particles of the hydrogenation component to be applied to the same support material. It is also possible for the separate components to be applied to separate, possibly different, support materials, which are then mixed with each other.

It is not clear an what mechanism the activity of the catalyst according to the invention is based. A possible explanation could be that due to the homogeneous distribution and the resultant very small mutual distance between the hydrogenation component and the metal-oxide containing component, the sulfur atoms which are released from the molecules of the sulfur containing compound at the surface of the particles of the hydrogenation component are allowed to migrate to and react with a neighbouring metal oxide particle under the influence of $H_2$. Metal oxide is then converted to a corresponding sulfide.

The catalyst according to the invention can be prepared in different ways using known per se techniques. Examples of such techniques are the application of the active component and/or components or precursors thereof to the support material by means of impregnation or precipitation, followed by drying and, if necessary conversion to a catalytically active material. The step mentioned last may for instance comprise calcining the dried material followed by reducing the calcined material. It is possible to apply, dry and calcine the hydrogenation component and the metal-oxide containing component one by one, or simultaneously, after which the material is finally reduced. Another way of making the catalyst according to the invention comprises the separate preparation of a support material with a hydrogenation component applied to it and a (optionally different) support material with a metal-oxide containing component applied to it. When the loaded support material particles are sufficiently small, by mixing a catalyst is obtained which satisfies all requirements of the invention.

The catalyst may be used in various forms, such as powder, pellets or extrusions. What form is chosen depends on the nature of the reaction and the type of reactor that is used.

The process according to the invention comprises in its most general sense reactions in which hydrogenation and/or dehydrogenation occurs. Examples of such reactions are inter alia the hydrogenation of benzene, "white oils" and solvents.

The process according to the invention can be carried out in various types of reactors which are suitable for hydrogenation and/or dehydrogenation, such a solid bed reactors, fluid bed reactors, trickle-phase reactors and the like.

In practice the process according to the invention is particularly important when feedstocks are used which contain a quantity of sulfur compounds, such as $H_2S$, mercaptans and thiophenes, because then pre-treatment of the feedstock can be omitted, and also no guard bed is needed. Moreover it is now possible for feedstocks which have a higher content of sulfur compounds to be hydrogenated or dehydrogenated directly, without the lifetime of the catalyst being shortened substantially. More particularly the invention is of importance for feedstocks which contain more than 1–5 ppm sulfur compounds, in particular in the form of $H_2S$, mercaptans and thiophenes.

The invention is illustrated in and by the following examples.

Preparation I (catalyst A)

50 g aerosol 200 V, marketed by the firm of Degussa, was suspended in 3.5 l demineralized water of 21° C. To this suspension 86.87 g $NiCl_2.6H_2O$ and 79 g urea were added. The pH of this suspension was adjusted to 3.0 by means of concentrated HCl. With vigorous stirring (300 rpm) the temperature was raised to 90° C. After 20 hours the suspension was filtered and washed with 30 l demineralized water. The material was dried in air at 110° C. for 16 hours. From this dried material a sieve fraction of between 0.60–0.85 mm was made. The BET surface area of this material was 276 $m^2/g$. By treating this sieve fraction for at least 48 hours in a gas stream of 50 ml/min consisting as to 100% of H at a temperature of 450° C., catalyst A was obtained having a specific nickel surface area of 19.1 $m^2$/Ni/gCat (71 $m^2$ Ni/gNi), as was measured by $H_2$ chemisorption.

Preparation II 50 g Kieselguhr was suspended in 2.5 l demineralized water of 25° C. The pH of this suspension was raised to 5.5 by means of concentrated HCl. In 1 l demineralized water 168.11 g $FeCl_3.6H_2O$ was dissolved. With vigorous stirring (300 rpm) this solution was injected into the suspension at a constant rate. During the injection the pH of the suspension was maintained between 5.45 and 5.55 by means of injection of an alkaline solution. Then the suspension was filtered and washed with 30 l demineralized water. The material was dried in air at a temperature of 110° C. for 16 hours.

Preparation III (catalyst B)

35.7 g of a material synthesized according to Preparation I was redispersed in 2 l demineralized water after washing and filtering. To this suspension an amount of 25 g aerosol 200 V, marketed by the firm of Degussa, was added with vigorous stirring (300 rpm). 17.9 g of the material described in preparation II was also added to the suspension described above after redispersion in 2 l demineralized water. The total suspension was homogenized for 6 hours with vigorous stirring (600 rpm). Then the suspension was filtered and washed with 30 l demineralized water. The material was dried in air for 16 hours at a temperature of 110° C. From this dried material a sieve friction of between 0.60–0.85 mm was made. The BET surface area of this material was 229 $m^2/g$. By treating this sieve fraction in a gas stream of 50 ml/min consisting as to 100% of $H_2$ at a temperature of 450° C. for at least 48 hours, catalyst B was obtained having a specific nickel surface area of 9.7 $m^2$ Ni/gCat (70 $m^2$ Ni/gNi), as determined by $H_2$ chemisorption.

Preparation IV (catalyst C)

71.4 g of a material synthesized according to Preparation I, after washing and filtering, was redispersed in 2.5 l demineralized water of 21° C. The pH of this suspension was raised to 5.5 by means of concentrated HCl. In 1 l demineralized water 148.2 g $FeCl_3.6H_2O$ was dissolved. In 1 hour this solution was injected into the suspension at a constant rate with vigorous stirring (300 rpm). During this injection the pH of the suspension was maintained between 5.45 and 5.55 by means of injection of an alkaline solution. Then the suspension was filtered and washed with 30 l demineralized water. The material was dried in air at a temperature of 110° C. for 16 hours. The BET surface area of this material was 319 $m^2/g$. From this dried material a sieve fraction of between 0.60–0.85 mm was made. By treating this sieve fraction in a gas stream of 50 ml/min consisting as to 100% of $H_2$, at a temperature of 450° C. for 48 hours, catalyst C was obtained having a specific nickel surface area of 1.7 $m^2$ Ni/gCat (8 $m^2$ Ni/gNi) as was determined by $H_2$ chemisorption.

EXAMPLE I

Sulfur resistance of the catalysts A, B and C

To determine the activity and lifetime of the catalysts A, B and C, as a test reaction the hydrogenation of benzene to cyclohexane was used:

$$C_6H_6 + 3H_2 \rightarrow C_6H_{12}$$

The reaction was performed by passing a feed gas of 37 ml/min $H_2$ with 8.4 vol. % benzene through a reactor with 1.5 ml of catalyst. The activity of the catalysts during the sulfur poisoning was measured in the temperature range of 200°–250° C. The activity is calculated as follows:

$$act(\%) = 100\% \left[ 1 - \frac{C_2}{C_1} \right]$$

wherein $C_1$ is the benzene partial pressure upstream of the reactor and $C_2$ is the benzene partial pressure downstream of the reactor.

During the hydrogenation of benzene various sulfur containing components, such as $H_2S$, $CH_3SH$ and $C_4H_4S$ were separately injected into the gas stream described above. These injections were performed using a pneumatically driven pulse valve with an accurately calibrated pulse volume.

The addition of $H_2S$ was performed by injecting a pulse loop volume of 10.25 ml containing 2 vol. % $H_2S$ in $H_2$ into the feed gas every 22.5 min. The same procedure was followed in the experiments with methyl mercaptan, CHSH, although the injection frequency was now 1 pulse loop volume per 18 min. In the experiments with thiophene, $C_4H_4S$, every 18 min a pulse loop volume of 0.56 ml, containing 4% $CH_4H_4S$ in $H_2$, was injected into the feed gas.

Figure 2:
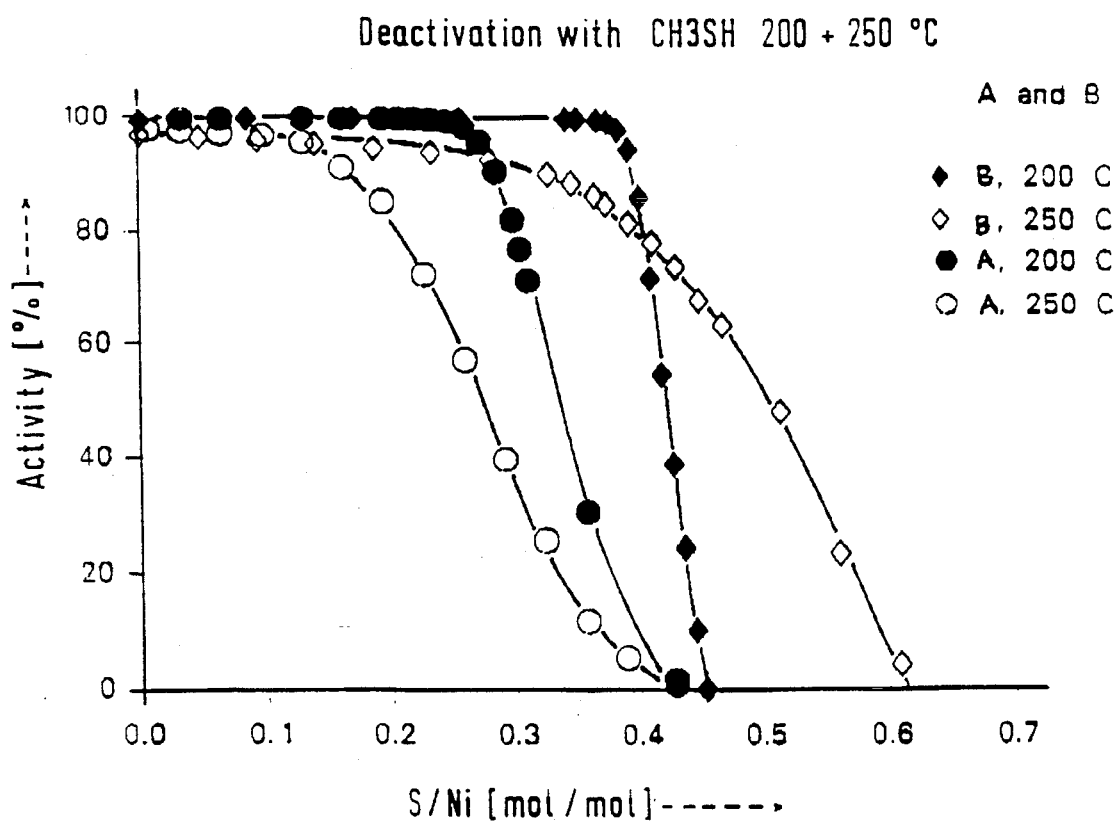
Figure 3:
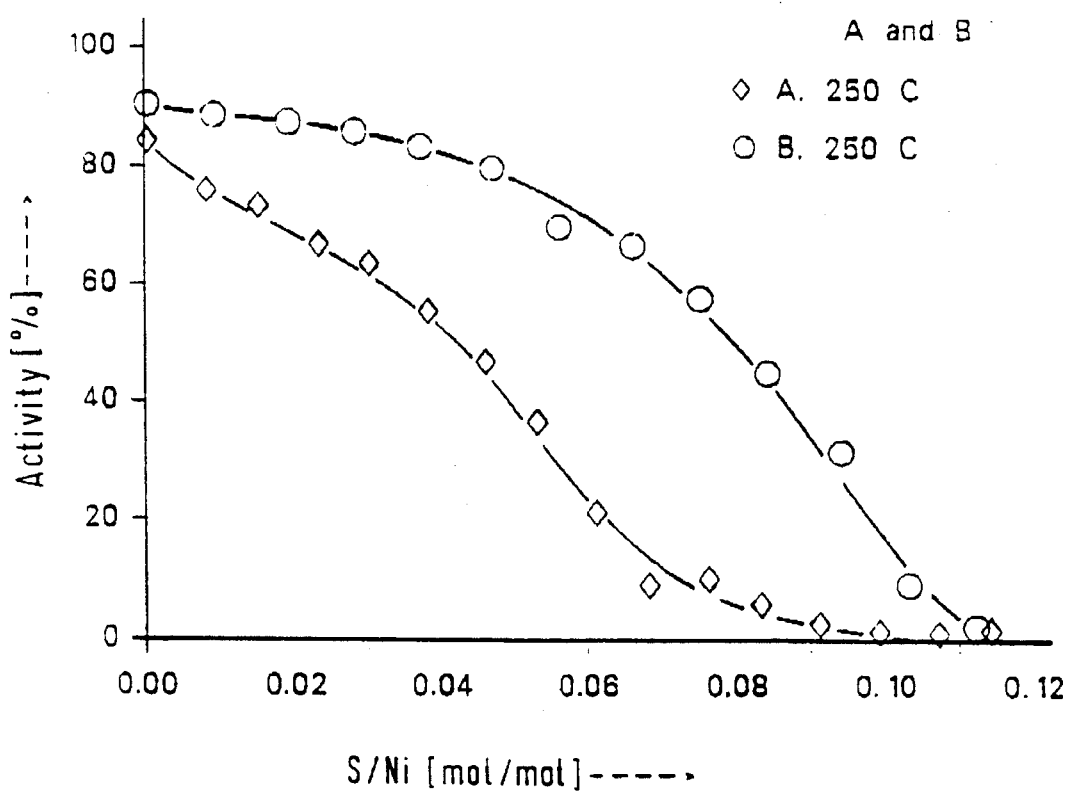

The results of the activity measurements are graphically shown in FIGS. 1, 2 and 3.

In each of these figures the activity of the catalyst, as defined hereinabove, is plotted as a function of the quantity of sulfur (in moles), passed through the reactor per mole of the nickel present in the catalyst.

FIG. 1: experiments with $H_2S$, 200° C.; catalysts A, B and C;

FIG. 2: experiments with $CH_3SH$, 200° and 250° C., catalysts A, B and C;

FIG. 3: experiments with $C_4H_4S$, 200° C., catalysts A and B.

FIG. 1 clearly shows that applying iron oxide to the catalyst systems has a strongly positive influence on the lifetime of the catalysts. The degree of HS resistance depends on the total amount of iron oxide present in the system; catalyst C comprises more iron oxide than catalyst B.

FIG. 2 clearly shows that, also with mercaptan being present in the feedstock, catalyst B exhibits a better resistance against sulfur poisoning, both at 200° and at 250°.

FIG. 3 clearly shows that at 250° C. catalyst B also exhibits greater resistance against sulfur poisoning than catalyst A, when thiophene is present in the feedstock as a sulfur containing component.

EXAMPLE II

In order to compare the activity of the catalyst according to the invention with known systems consisting of a mixture of a hydrogenation catalyst on a support and a sulfur binding component, such as an iron compound (mixed bed), or consisting of a so-called guard bed, some experiments have been performed with thiophene at 250° C.

A guard bed is a catalyst bed the upper part of which consists of 0.10 g of a sieve fraction of between 0.60–0.85 mm of a catalyst prepared according to Preparation II. The lower part of the catalyst bed consists of 0.21 g of a sieve fraction of between 0.60–0.85 mm of a catalyst prepared according to Preparation I (catalyst A). The system thus obtained has an Fe/Ni ratio of 0.77 which is identical to the Fe/Ni ratio of the catalyst prepared according to Preparation III (catalyst B).

A mixed bed comprises a physical mixture of 0.10 g of a sieve fraction of between 0.60–0.85 mm of a catalyst prepared according to preparation II and 0.21 g of a sieve fraction of between 0.60– 0.85 mm of a catalyst prepared according to Preparation I (catalyst A). The system thus obtained has an Fe/Ni ratio of 0.77, which is identical to the Fe/Ni ratio of the catalyst prepared according to Preparation III (catalyst B). The two catalyst systems thus obtained will be referred to as Gua 0.77 and Mix 0.77, respectively. The flow of the benzene (8.3 vol. %)/hydrogen mixture was arranged in the so-called "down-flow" configuration. The volume of the two catalyst systems mentioned was 1.5 ml.

Figure 4:
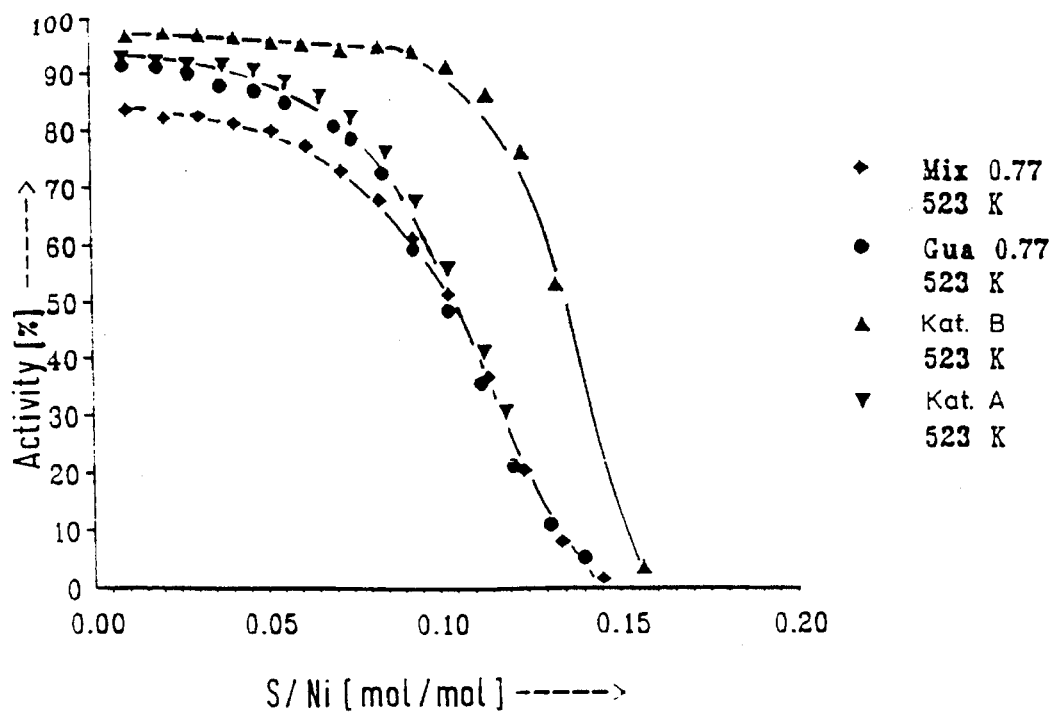

The results of the experiments are shown in FIG. 4.

The experiments were performed in the same way as in Example I. Compared were a guard bed, a mixed bed, catalyst A and catalyst B. All systems had the same iron/nickel ratio, with the exception, of course, of catalyst A, which did not contain iron.

The results of FIG. 4 show very clearly that the results of catalyst A, the guard bed and the mixed bed do not differ strongly when poisoned with thiophene at 250° C. (523 K). Only the catalyst according to the invention exhibits a clearly better resistance against this poisoning.

We claim:

1. A process for the hydrogenation and/or dehydrogenation of a feedstock containing one or more sulfur containing compounds, comprising providing a feedstock containing at least one sulfur containing compound; and carrying out hydrogenation and/or dehydrogenation of said feedstock in the presence of a non-sulfided catalyst having an improved resistance against deactivation by sulfur compounds, said catalyst comprising at least one free metal hydrogenation component, at least one metal-oxide containing component and at least one component acting as a support material, in which at least a part of the hydrogenation component as well as at least part of the metal-oxide containing component are present on said support material as separate particles, the particles of the hydrogenation component and the particles of the metal-oxide containing component being homogenously distributed in the catalyst.

2. The process of claim 1 wherein in said providing step, said at least one sulfur containing compound in said feedstock is selected from a group consisting of hydrogen sulfide, mercaptan, and thiophene.

3. The process of claim 1 wherein in said providing step, said at least one sulfur containing compound in said feedstock is present at a concentration of greater than 1–5 ppm.

4. The process of claim 1 wherein the composition of said catalyst per $mm^3$ is not essentially different from the total composition of said catalyst.

5. The process of claim 1 wherein the composition of said catalyst per 0.01 $mm^3$ is not essentially different from the total composition of said catalyst.

6. The process of claim 1 wherein in said catalyst the hydrogenation component is copper.

7. The process of claim 1 wherein in said catalyst the hydrogenation component is a metal selected from the group consisting of nickel, platinum, palladium, rhodium, cobalt, ruthenium and mixtures of two or more of these metals.

8. The process of claim 1 wherein in said catalyst the hydrogenation component is nickel.

9. The process of claim 1 wherein in said catalyst the metal-oxide containing component is an oxide of a metal selected from the group consisting of silver, lanthanum, antimony, nickel, bismuth, cadmium, lead, tin, vanadium, calcium, strontium, barium, cobalt, copper, tungsten, zinc, molybdenum, manganese, iron and mixtures of two or more of these metals.

10. The process of claim 1 wherein in said catalyst the metal-oxide containing component is one or more oxides of iron.

11. The process of claim 1 wherein in said catalyst the average size of the particles of the support material, which may or may not be porous, is between 0.001 and 200 μm.

12. The process of claim 1 wherein in said catalyst the average size of the particles of the support material, which may or may not be porous, is between 0.005 and 150 μm.

13. The process of claim 1 wherein in said catalyst the support material is selected from the group consisting of aluminum oxide, silicon oxide, silicon oxide-aluminium oxide, titanium dioxide, zirconium dioxide, magnesium oxide, mixtures of two or more of these materials, and active carbon.

14. The process of claim 1 wherein said catalyst comprises 5–99.9 wt. % support material calculated on the total weight of the support material and the hydrogenation component in reduced form.

* * * * *

UNITED STATES PATENT AND TRADEMARK OFFICE
CERTIFICATE OF CORRECTION

PATENT NO. : 5,482,616
DATED : January 9, 1996
INVENTOR(S) : Nilanjan Brahma, et al.

It is certified that error appears in the above-indentified patent and that said Letters Patent is hereby corrected as shown below:

Column 4, line 10, "an what mechanism", should read --on what mechanism--.

Column 5, line 1, "50 g aerosol", should read --50 g Aerosil--.

Column 5, line 29, "25 g aerosol", should read --25 g Aerosil--.

Column 6, line 28, "CHSH,", should read --$CH_3SH$,--.

Column 6, line 32, "$CH_4H_4S$", should read --$C_4H_4S$--.

Signed and Sealed this

Eleventh Day of August 1998

Attest:

BRUCE LEHMAN

Attesting Officer

Commissioner of Patents and Trademarks